(12) United States Patent
Dantler

(10) Patent No.: US 8,813,540 B2
(45) Date of Patent: Aug. 26, 2014

(54) ANALYSIS METHODS AND DEVICES FOR FLUIDS

(75) Inventor: Markus Dantler, Thalwil (AT)

(73) Assignee: MaxDeTec AG, Thalwil (CH)

( * ) Notice: Subject to any disclaimer, the term of this patent is extended or adjusted under 35 U.S.C. 154(b) by 260 days.

(21) Appl. No.: 13/254,030

(22) PCT Filed: Mar. 3, 2010

(86) PCT No.: PCT/IB2010/000436
§ 371 (c)(1),
(2), (4) Date: Aug. 31, 2011

(87) PCT Pub. No.: WO2010/100549
PCT Pub. Date: Sep. 10, 2010

(65) Prior Publication Data
US 2011/0314902 A1    Dec. 29, 2011

(30) Foreign Application Priority Data
Mar. 5, 2009   (DE) .......................... 10 2009 011846

(51) Int. Cl.
*G01N 37/00* (2006.01)
*G08B 21/00* (2006.01)
*G01N 15/02* (2006.01)
*G01N 1/22* (2006.01)
*G01N 1/14* (2006.01)
*G01N 1/26* (2006.01)
*G01N 15/06* (2006.01)
*G08B 17/10* (2006.01)

(52) U.S. Cl.
CPC .......... *G01N 1/2211* (2013.01); *G01N 15/0255* (2013.01); *G01N 1/14* (2013.01); *G01N 1/26* (2013.01); *G01N 15/06* (2013.01); *G08B 17/10* (2013.01); *G01N 2015/0693* (2013.01)
USPC ......................................... 73/28.01; 340/627

(58) Field of Classification Search
USPC .................... 340/628; 73/28.01, 31.01, 31.02
See application file for complete search history.

(56) References Cited

U.S. PATENT DOCUMENTS 2,033,466 A  *  3/1936  Grant, Jr. ..................... 340/524
3,334,516 A     8/1967  Cedrone
(Continued)

FOREIGN PATENT DOCUMENTS

DE       3430264 A1    2/1986
EP       0 015 991     7/1984
(Continued)

OTHER PUBLICATIONS

International Search Report for corresponding International Application No. PCT/IB2010/000436 mailed Sep. 24, 2010.
(Continued)

*Primary Examiner* — Hezron E Williams
*Assistant Examiner* — Nathaniel Kolb
(74) *Attorney, Agent, or Firm* — Renner, Otto, Boisselle & Sklar, LLP

(57) ABSTRACT

The invention relates to novel methods and to devices for a measuring and analysis apparatus that measures impurities and/or particles in a gas or air. In a particle separation step, target particles having predetermined particle properties are separated from remaining particles from a gas or gas mixture such as air or a liquid, in short a fluid, that contains a particle mixture, and the occurrence and/or frequency of said target particles is determined in a measuring chamber. The likewise novel cooling of the radiation sources required for measurement permits the use of such having high power, as is required for measuring few particles or the smallest impurities. A further novel expansion of the electrical measurement range allows small but also abundant particles and impurities to be measured. In addition, a novel interface simplifies the start-up of the apparatus.

19 Claims, 11 Drawing Sheets

(56) References Cited

U.S. PATENT DOCUMENTS

Figure 1:
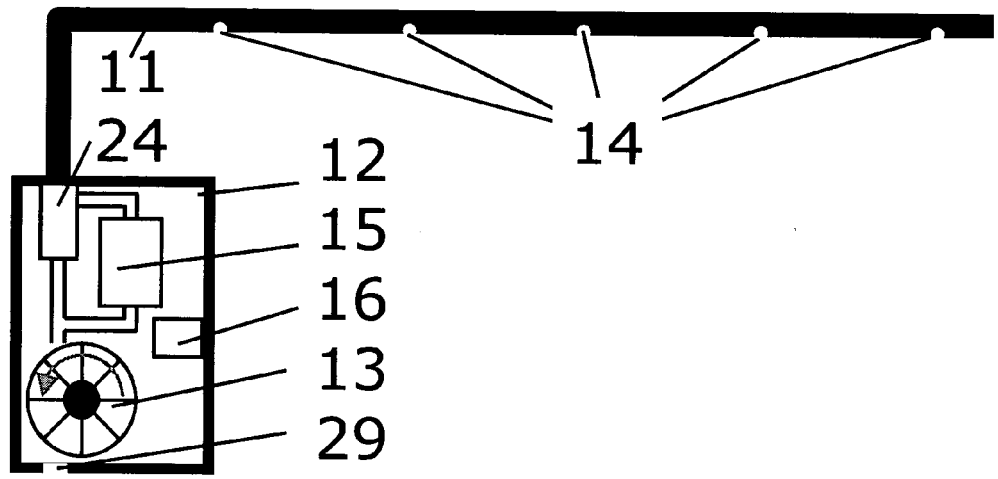

| | | | |
|---|---|---|---|
| 4,035,788 | A | 7/1977 | Barr |
| 5,412,975 | A | 5/1995 | Raabe et al. |
| 5,481,357 | A | 1/1996 | Ahsan et al. |
| 5,625,321 | A * | 4/1997 | Sasaki et al. ............. 330/124 R |
| 5,999,250 | A | 12/1999 | Hairston et al. |
| 6,111,630 | A * | 8/2000 | Watanuki et al. ............. 349/161 |
| 6,688,187 | B1 | 2/2004 | Masquelier |
| 7,536,914 | B2 * | 5/2009 | Land et al. ...................... 73/705 |
| 2006/0054017 | A1 | 3/2006 | Haglund et al. |
| 2007/0014060 | A1 * | 1/2007 | Land et al. ...................... 361/42 |
| 2007/0139649 | A1 | 6/2007 | Siemens |
| 2009/0025453 | A1 * | 1/2009 | Griffith et al. ............... 73/31.02 |

FOREIGN PATENT DOCUMENTS

| | | |
|---|---|---|
| WO | 02/095705 A1 | 11/2002 |
| WO | 2005/043479 A1 | 5/2005 |
| WO | 2005/071390 A1 | 8/2005 |
| WO | 2008/118769 A1 | 10/2008 |

OTHER PUBLICATIONS

International Preliminary Report on Patentability and Written Opinion for corresponding International Application No. PCT/IB2010/000436 mailed Sep. 20, 2011 (English Translation).

* cited by examiner

| (T100) | (T103) | (T104) |
|---|---|---|
| 1 | 1'000 | 100 |
| 2 | 2'000 | 200 |
| 3 | 3'000 | 300 |
| 4 | 4'000 | 400 |
| 5 | 5'000 | 500 |
| 6 | 6'000 | 600 |
| 7 | 7'000 | 700 |
| 8 | 8'000 | 800 |
| 9 | 9'000 | 900 |
| 10 | 10'000 | 1'000 |
| 11 | 10'000 | 1'100 |
| 12 | 10'000 | 1'200 |
| 20 | 10'000 | 2'000 |
| 50 | 10'000 | 5'000 |
| 100 | 10'000 | 10'000 |
| 110 | 10'000 | 10'000 |

Fig. 7

|    | 130        |            |            |
|----|------------|------------|------------|
|    | 5.00 %/m   | 8.00 %/m   | 2.00 %/m   |
| 1  | 5.00 %/m   | 8.00 %/m   | 2.00 %/m   |
| 2  | 2.50 %/m   | 4.00 %/m   | 1.00 %/m   |
| 3  | 1.67 %/m   | 2.67 %/m   | 0.67 %/m   |
| 4  | 1.25 %/m   | 2.00 %/m   | 0.50 %/m   |
| 5  | 1.00 %/m   | 1.60 %/m   | 0.40 %/m   |
| 6  | 0.83 %/m   | 1.33 %/m   | 0.33 %/m   |
| 7  | 0.71 %/m   | 1.14 %/m   | 0.29 %/m   |
| 8  | 0.63 %/m   | 1.00 %/m   | 0.25 %/m   |
| 9  | 0.56 %/m   | 0.89 %/m   | 0.22 %/m   |
| 10 | 0.50 %/m   | 0.80 %/m   | 0.20 %/m   |
| 15 | 0.33 %/m   | 0.53 %/m   | 0.13 %/m   |
| 20 | 0.25 %/m   | 0.40 %/m   | 0.10 %/m   |
| 30 | 0.17 %/m   | 0.27 %/m   | 0.07 %/m   |
| 40 | 0.13 %/m   | 0.20 %/m   | 0.05 %/m   |
| 131 | 132       | 133        | 134        |

Fig. 9

ANALYSIS METHODS AND DEVICES FOR FLUIDS

FIELD OF TECHNOLOGY

The present invention relates to novel methods and corresponding measuring and analysis devices that measure pollutants or particles in a fluid, thus a gas, gas mixture, for example air, or a liquid. The invention, on one hand, relates to a method and an arrangement for particle separation, wherein in a gas or a liquid comprising a particle mixture target particles with predetermined properties are separated from residual particles. The target particles themselves are analyzed and measured. In addition to the particle separation in measuring and analysis devices, the invention through a novel cooling mechanism enables the employment of radiation sources with very high power such as are necessary for the measurement of a small number of particles or of extremely small pollutants. In addition, an expanded electrical measuring range permits the determination of low but also of relatively high occurrences of particles and pollutants. A novel user interface, additionally, simplifies the initial operation of such devices.

BACKGROUND AND PRIOR ART

Inherent in currently available measuring and analysis devices for pollutants or particles in a fluid, e.g. a gas, gas mixture or a liquid, and the corresponding measuring and analysis methods are a number of problems.

A first problem area involves particle separation. In several applications, for example, only particles having a certain size are of significance and only these are supposed to reach a measuring chamber, e.g. the initially present particle mixture must be separated according to specific particle properties. This particle separation has been found to be difficult, in particular if the mixture involves microscopically small particulate matter. This will be explained using some examples.

A task occurring frequently in industrial, technical but also biological or medical investigations, for example in diagnoses, includes the separation of gases or suspension mixtures by distributing or sorting microparticles from a large starting quantity into specific groups, each with like properties. If there is success in conducting only the desired target particles to the measuring chamber or the measuring region by means of particle separation, the following advantages are obtained:
1. Increase of the operating reliability of the device due to few or no erroneous measurements through particles that do not correspond to the target particles.
2. Extension of the device life due to lesser or prevented dirt deposits of larger particles on the optical measuring or analysis instrument.
3. Simplification of the device since protective components, for example filters, or measurement components measuring the larger particles can be omitted.

Using an exemplary application case, the detection and measurement of extremely small quantities of fire aerosol particles will be considered as occur in so-called Aspirating Smoke Detectors (ASD). In this case the air of the space to be monitored is aspirated through a pipe system. This pipe system is comprised of one or also several pipes most frequently having a total length of between 10 and 200 m. At intervals of approximately 4 m it has aspiration ports with a diameter of approximately 2 to 6 mm. This can be used to monitor, for example, a warehouse, an IT computing center, a manufacturing area or electrical switchgear equipment. The measuring chamber in the device subsequently measures the occurrence of fire aerosol particles and, upon reaching a specific, previously set value, outputs an alarm signal.

Fire aerosol particles have a size between approximately 0.01-10 µm. Viruses, for example, would be smaller particles and dust larger particles. In order to be able to detect extremely small quantities of fire aerosol particles, a highly sensitive measuring chamber is necessary. Here, radiation such as light is emitted by a light source into a detection area. If in this area such small fire aerosol particles are located, they scatter the light. This effect causes on a photoelectric sensor either light obscuration (transmission measurement) since less light occurs [sic: is incident] in this case, or it is only through the light scattering that light reaches the sensor (reflection measurement). The fine particles are detected using one of these two principles. A light emitting diode (LED), a laser diode (LD), a Xenon lamp or the like can be utilized as the radiation source. Other parts can also be located in the measuring chamber, for example optical lenses, one or several photoelectric sensors and/or also an amplifier circuit.

Another capability for detecting fire aerosol particles is the use of an ionization chamber.

In the following by example currently utilized methods and means as examples of particle separation or sequestration will be described.

It should also be explained that here by "particle separation" is understood the separation of particles according to predetermined particle properties, wherein the separated particles in principle always remain in the fluid, e.g. in separate volumes of the fluid. In contrast, by "particle sequestration" is here understood the removal of the undesired particles from the fluid.

One method is sedimentation by gravity, centrifugal force or diversion, such as is employed for example in cyclone separators. The devices utilized here are relatively large and most often complicated and expensive to manufacture, which limits their use as wall or table devices. In addition, particle sequestration in certain applications, and especially in sizes in the micrometer range, is not good enough. The problem lies here in the principle since a sequestration of particles for measurement is actually not necessary. Only these or certain particles must not reach the measuring region, however they can remain in a stream outside of the measuring region. These devices intend to sequester the particles out of a gas and consequently the entire fluid would subsequently be free of these pollutants. Relatively large particles can remain in the main stream. It suffices if from the fluid only a small quantity without pollutants is branched off. Particle sequestration or deposition is not necessary at all, and therefore emptying and cleaning the cyclone separator or a filter exchange, etc. becomes superfluous.

In electrostatic sequestration the particles are electrostatically charged and deflected in an electric field. Disadvantages here are the additional necessary electrical parts and the moisture sensitivity of this variant, which limits its application.

In particle sequestration by filters, for example filter mats, fabric filters, etc., relatively large particles are retained on their entry into the device or into the measuring chamber. However, a disadvantage of such filters is that they cause a pressure drop. The aspiration mechanism, for example a ventilator, must therefore be correspondingly powerful, which, in turn, entails a higher energy requirement. But a further and far more serious disadvantage of these filters is that during operation they become progressively clogged by the retained particles. Stated differently, progressively fewer of the target particles to be measured can pass through the filter. In an extreme case a blocked filter prevents the desired target particles from reaching the measuring region at all. In a fire detector as described above the fire aerosol particles, which, in fact, are the particles to be measured, can no longer flow into the measuring chamber. In the event of danger, such a device would only inadequately be capable of detecting or they would detect nothing, e.g. the fire detector would not indicate anything at all. This requires regular filter exchanges since clogging of the filter, and therewith the blockage of the inflow into the measuring chamber, cannot be predicted.

As a further feasibility the occurrence of undesired, for example, relatively large particles can also be determined by means of an additional, for example optical, measuring method. A disadvantage here is that the measuring chamber becomes polluted through dirt deposits especially by larger particles, more electrical components are required and the setting and calibration of the device entails additional expenditures and effort.

Alternatively, it is also feasible to accept the dirt deposits of the measuring chamber and to utilize electrical or electronic measures for the correction of the measurement results. If the optical measuring components take up particles during operation in progress, e.g. become dusty, their sensitivity is reduced. As compensation the sensitivity of the measuring system is electronically corrected or readjusted. This electronic readjustment is referred to as "drift compensation". For example, in time the response behavior becomes more sensitive since there is the assumption that the optical parts pick up (dirt) particles, with less light reaching the measuring chamber and the measuring sensor. Whether there are, in fact, dirt deposits present or whether such pollution is heavier or lighter, is irrelevant for the so-to-speak "planned", e.g. preset compensation. However, there is a serious disadvantage of this drift compensation results, namely that the measuring behavior, and thereby also the response behavior, of the device, for example the fire detector, changes in the course of operation and this change does not correlate with the actual sensitivity or the extent of dirt deposits.

Some of said methods are described using by example a fire detector disclosed in the published application WO 2005/043479 A1. Described in this application, for example, is a method of the manner in which differentiation of particles according to their size can take place.

In the published U.S. application 2009/0025453 are described a smoke detector device and the corresponding method, in which a side stream with smaller particles is branched off a main stream by dividing the main stream into two substreams and accelerating it. The greater inertia of the larger particles causes them to continue moving in a straight forward path, while the smaller particles are more easily diverted into a side stream. This mechanical principle, known per se, of separation by inertia/gravity is here utilized inter alia in a smoke detector in such manner that an air stream is accelerated in a duct assembly. Within the duct is located a port with low pressure that aspirates the smaller particles and thus effects the separation. However, the design of this device is highly complex, especially since the aspiration mechanism is located within the duct and forms a part thereof. The manner in which the depicted structure is to prevent reflected larger particles from also reaching the side stream intended for investigation is also not apparent. The problem areas listed in the following are also not addressed at all in this US application.

The second problem area relates to the accumulation of particulate matter in the measuring chamber, in particular on the optical or electronic components used for the measurement. These components are located in a region through which the medium flows, e.g. the gas or the liquid. As soon as additional parts, or the necessary openings into the measuring chamber or the flow region, are inserted, for example, lenses, sensors, radiation sources, etc., unevennesses are formed, such as gaps and openings for the radiation source or the sensor. These result in turbulences of the flowing medium which, in turn, leads to accumulations of particulate matter, most often at undesirable sites.

Should such accumulation be deposited on the optical components, in particular at or on the radiation source, the result would be that less radiation emitted by the radiation source reaches the measuring region. This alone already distorts the measurement. The same applies to the sensor. If particles collect on its surface or those of its components, for example lenses, its sensitivity, and therefore its capability of enabling correct measurements, is reduced. Stated differently, the particle accumulation prevents the ultimate objective of flawless measurements.

A known method for preventing such accumulation involves virtually filtering all particles, including the target particles, out of the medium by means of a separate upstream fine filter and thereby generating a quasi-pure fluid. This fluid subsequently flows over the radiation source as well as also over the sensor. It prevents particles from collecting on these two parts or in their proximity. This pure gas subsequently joins the main stream again. The disadvantages of a filter were already explained above. The extent of dirt deposits and clogging cannot be determined, and consequently also not the time when the filter becomes clogged, resulting in the gas/air inflow into the measuring chamber being reduced or blocked. The consequences, for example in a fire detector, can be fatal if a fire hazard is detected too late or not at all.

The present invention addresses the problem of avoiding the above disadvantages of known methods and arrangements with respect to the first problem area and to ensure a simple and operationally reliable separation of the particles in a fluid intended for measurement. This problem is resolved through measures and means defined in the patent claims, wherein advantageous embodiments and applications of the invention are in particular evident in the dependent patent claims.

The particle separations according to the invention and described in the following are improved separation methods that are distinguished by high throughput, high selectivity and discriminatory power and cost-effective manufacture, and avoid the disadvantages of the above listed current methods. The same applies to the disclosed separation means for implementing such methods.

With the particle separation according to the invention, furthermore, the above problem of accumulations in the measuring chamber, in particular on the optical or electronic components serving for the measurement, is eliminated or at least reduced. Through the separation, in general, the particle content of the medium to be measured is reduced, whereby generally the penetration of relatively large particles into the measuring region is prevented and dirt deposits on parts, such as the radiation source and/or on the sensors, are reduced. The smaller target particles which, nevertheless, may potentially still accumulate, represent a significantly lesser impairment.

A third problem area in the measuring and analysis methods and devices under discussion here relates to the light or radiation source that is disposed in or on the measuring chamber and with the aid of which the measurement per se is carried out. This radiation source must output a corresponding power, for example light in the visible wavelength range, in order to enable the detection and measurement of extremely small quantities of very small particles. Here the problem is that the radiation source must produce high radiative power and this must be as constant as possible over as long a service life as is possible. Moreover, operation in a corresponding narrow and most often low temperature band is essential. Only in this way is it possible to ensure that the maximally possible service life is attained.

For this purpose the following methods are currently applied and these will be described by example.

Cooling bodies are so disposed that the heat generated by the light or radiation source is dissipated into the surrounding environment. It is understood that here an appropriate cooling body is necessary which, again, must be placed within the device or outside it. This requires construction efforts and complexity, and also makes the device more cumbersome and difficult to handle.

The light or radiation source is worked in pulsed operation, for example with 1 Hz or less. Thus the light source generates less heat and the cooling power can be reduced. However, continuous measurement is therefore not possible, and in particular individual peak values cannot be acquired.

For its cooling, the radiation source is placed in the fluid flow. But this method has the disadvantage that particles located in the fluid stream can collect on the radiation source. This, in turn, decreases the output radiative power which can be radiated into the measuring chamber. On the other hand, should the radiation source be placed in an area with reduced fluid flow the cooling power may not suffice, resulting in a decrease in the life of the radiation source.

Lastly, a radiation source with reduced power can be utilized. However, the measuring and detection capability of the device is thereby reduced.

The present invention also addresses the problem of avoiding the above disadvantages of known methods and arrangements with respect to the third problem area. This problem is resolved through measures and means such as are defined in the patent claims, wherein advantageous embodiments and applications of the invention are evident in particular in the dependent patent claims.

The disposition of the cooling unit according to the invention and presented here for the radiation source for measuring and analysis devices is suitable for avoiding the listed disadvantages of known dispositions and obtaining constant high radiative power over a long time period. It is also distinguished by a simple structure and thus cost-effective manufacture.

A fourth problem area relates to the size or bandwidth of the electrical measuring range of measuring and analysis devices of the type described here. In measuring extremely small particle quantities of, for example, fire aerosol particles, a radiation source, for example an LED, laser diode (LD), Xenon lamp, etc., emits its radiation into a measuring region. A highly sensitive photoelectric sensor with an electric amplifier circuit subsequently measures the radiation obscuration or the radiation reflection caused by particles located in the medium in the measuring chamber. The signal amplification, as a rule, takes place via several series connected transistors (Darlington circuits) or operational amplifiers.

In order for even small quantities of very small particles to be detectable, at least one, more often several, of the following preconditions must be met:
1. A measuring system with a very high signal-to-noise ratio (S/N ratio);
2. A radiation source with the requisite radiative power;
3. A high amplification of the sensor output signal in order to provide a signal that can be processed by the evaluation circuit, for example for a display.

However, the disadvantage of this characteristic is that, while extremely small quantities of particles can be measured at very high resolution, the electrical measuring range is very small. In certain application cases, not only extremely small quantities of particles are to be measured but in addition also an increased occurrence. Here, the measuring equipment fails since the electrical measuring range is being exceeded.

EP 0733894 discloses a possible solution for this problem. In this solution a sensor decreases the driver current supplied to the light source in order to set the sensitivity of the device to a lower level. The disadvantage here is that this control is complex and not necessarily linear, because from the activation of the light source up to the sensor which picks up the signal, there are too many components which negatively impact a linear measuring result due to their tolerances, ageing, etc.

Another feasibility employed is varying the gain of one or more amplifiers connected in series. For example, by means of a switch there is the capability of switching from one amplification value to another. Since with many amplifiers resistance values determine the amplification, it is feasible to switch by means of a mechanical switch, for example, from one resistance value to another and thereby change the gain of the circuit. This amplification can consequently be increased or also decreased. The disadvantage here is that it is necessary to switch over either manually or electronically, thus again requiring additional parts.

The present invention here also offers a resolution defined in the patent claims, wherein advantageous embodiments and applications of the invention are in particular evident in the dependent patent claims.

The presented circuit according to the invention, which amplifies the output signal of the sensor, has a very large amplification range without requiring manual switching and enables the automatic display of a very large bandwidth of measured values. It is distinguished by simple structure and thus cost-effective manufacture.

A fifth problem area in connection with analysis and measuring devices of said type is the interface for the basic setting and the initial operation of such a device, in particular of a fire detector. It does not require special imagination [to understand] that the erroneous setting of a fire detector can have catastrophic consequences.

As already described, for the detection and measurement of pollutants in air or other gases, devices are often employed which aspirate samples by means of an aspiration mechanism via a duct system, conduct these samples to a measuring chamber and analyze them here. The duct system is, as a rule, between 10 and 200 m long and most often has several aspiration ports, frequently with an opening diameter of 2 to 6 mm. Devices for the detection of fire aerosols are referred to as aspirating smoke detectors (ASD) and are widely utilized.

These devices must be installed on site and this installation process or initial operation is complicated, prone to error and an erroneous setting can, as stated, have catastrophic consequences.

It is prior art to set in the initial operation of aspirating smoke detectors the sensitivity of the measuring chamber or its electronic evaluation circuitry in units of % light obscuration/m. For example, frequently 0.5% light obscuration/m is set on the device at the time it is delivered. For the initial operation the requisite setting value must be determined on site and the setting must be corrected. However, this [value] itself does not provide any information about whether or not the device setting is a normal, high or highest sensitivity or how rapidly, for example, a fire danger is detected.

At the time of the setting a technician must first determine on site the desired target value for each aspiration port. For example if a response behavior is desired which is comparable to a conventional point detector, 5% light obscuration/m is selected. The technician must either know this value by heart, try and look it up or ask for it.

In the event of fire, in the least favorable case smoke with fire aerosols reaches only a single aspiration port and all other aspiration ports, as before, are reached only by (pure) air without fire aerosols. If the pipe system has a specific number of aspiration ports, the desired target value for each aspiration port must be divided by the number of aspiration ports. The result of the division must subsequently be set on the device. If, for example, a pipe system has six aspiration ports and the target value for each aspiration port is 5% light obscuration/m, then the value of 0.83% light obscuration is calculated, namely 5%:6=0.83%. This value must be set at the measuring chamber or its electronic evaluation circuitry. If fire aerosols cause 0.83% light obscuration/m in the measuring chamber, the device triggers an alarm signal.

This form of setting, as takes place in virtually all devices available on the market, requires a calculation which, while it is not particularly complicated, yet it is easily possible to make mistakes. The fatal consequences were also described above.

For this problem the present invention also offers a simple and practical solution by proposing an arrangement in which only the number of aspiration ports must be entered. This simple process is hardly prone to errors and therefore leads in so far as possible to reliable initial operation in particular of fire detectors (aspirating smoke detectors).

Details of the invention can be found in the patent claims and the following description of embodiment examples in conjunction with the drawing.

DESCRIPTION OF SEVERAL EMBODIMENT EXAMPLES

Figure 3A:
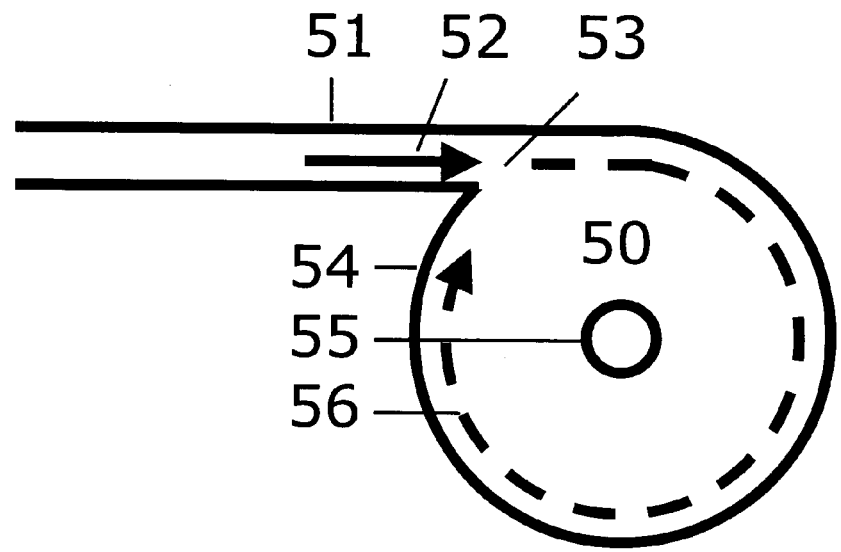
Figure 2A:
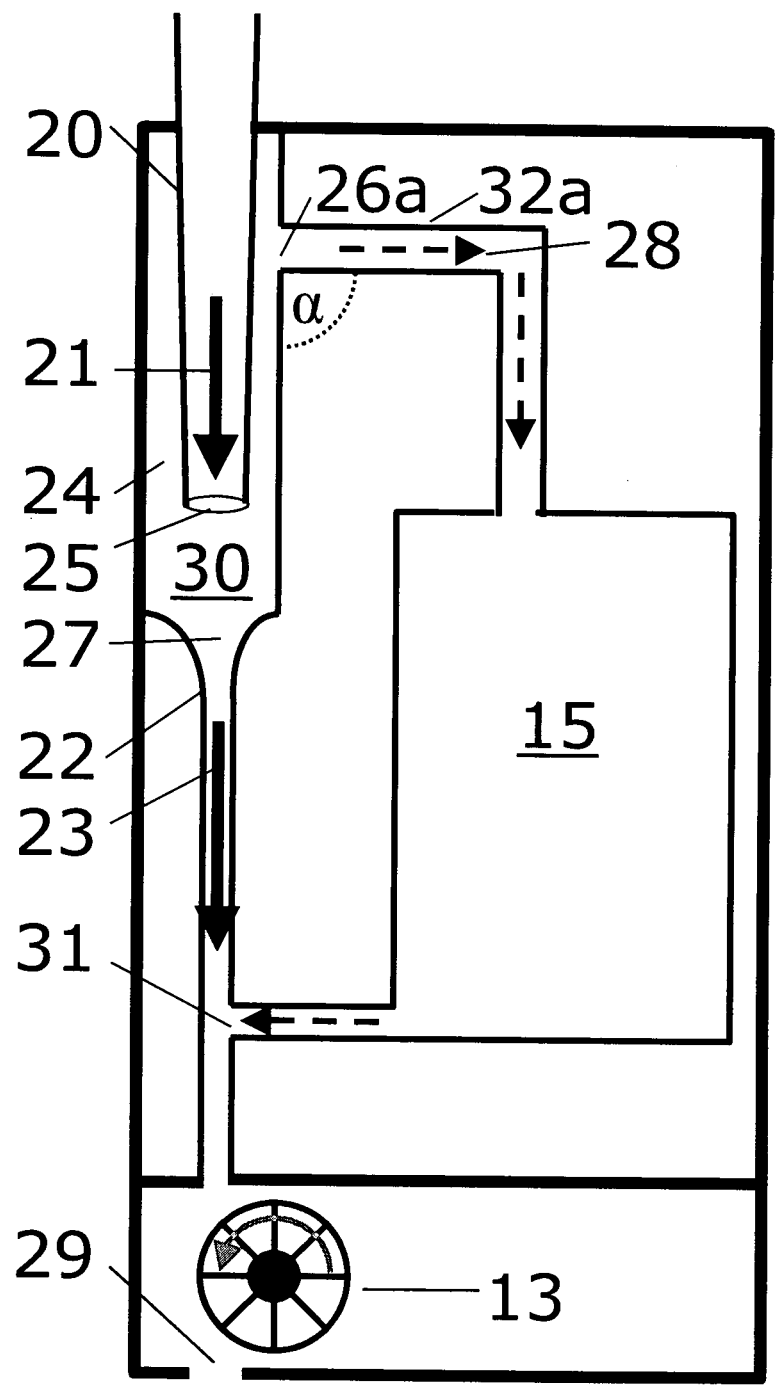
Figure 2B:
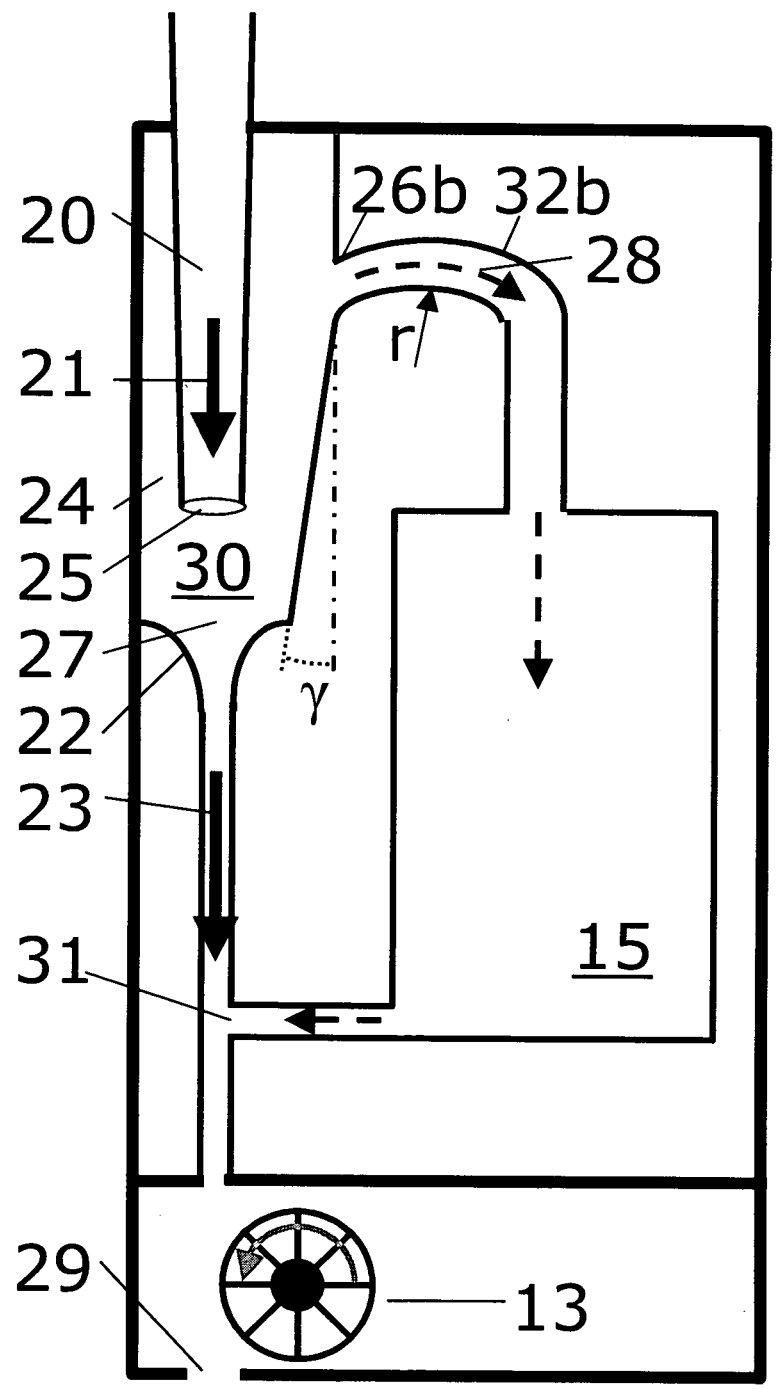
Figure 2C:
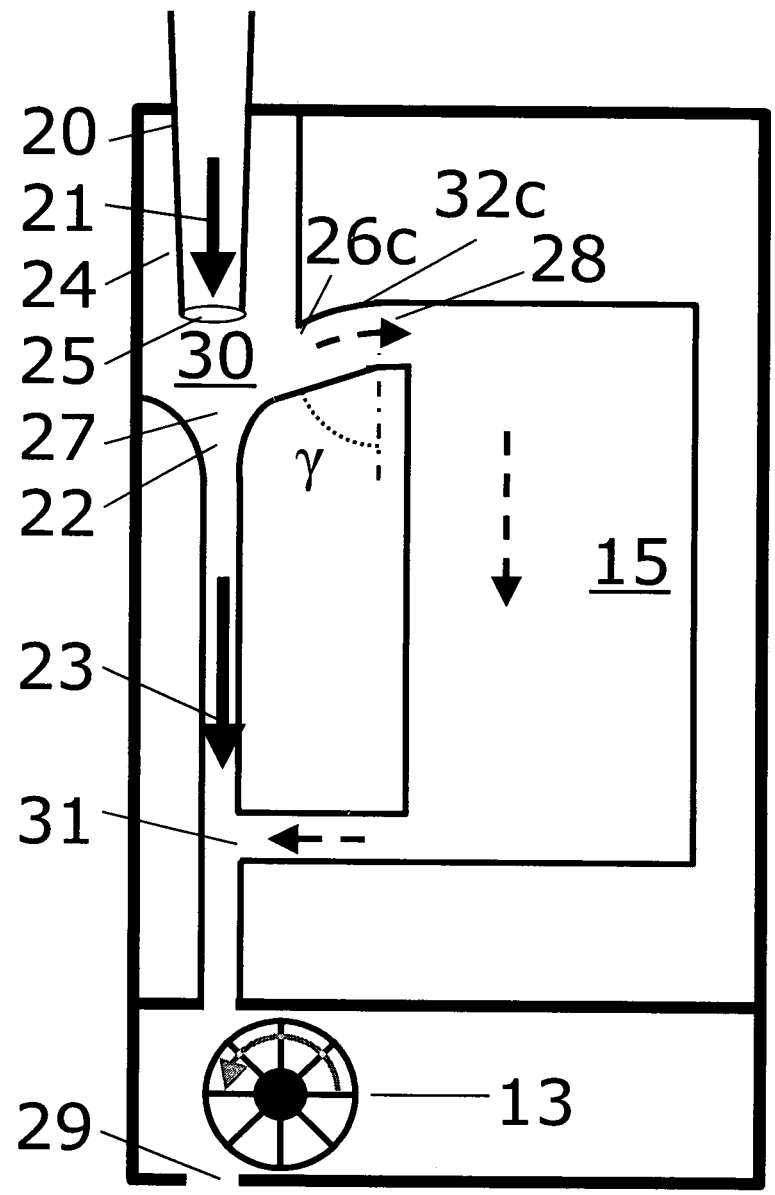
Figure 3B:
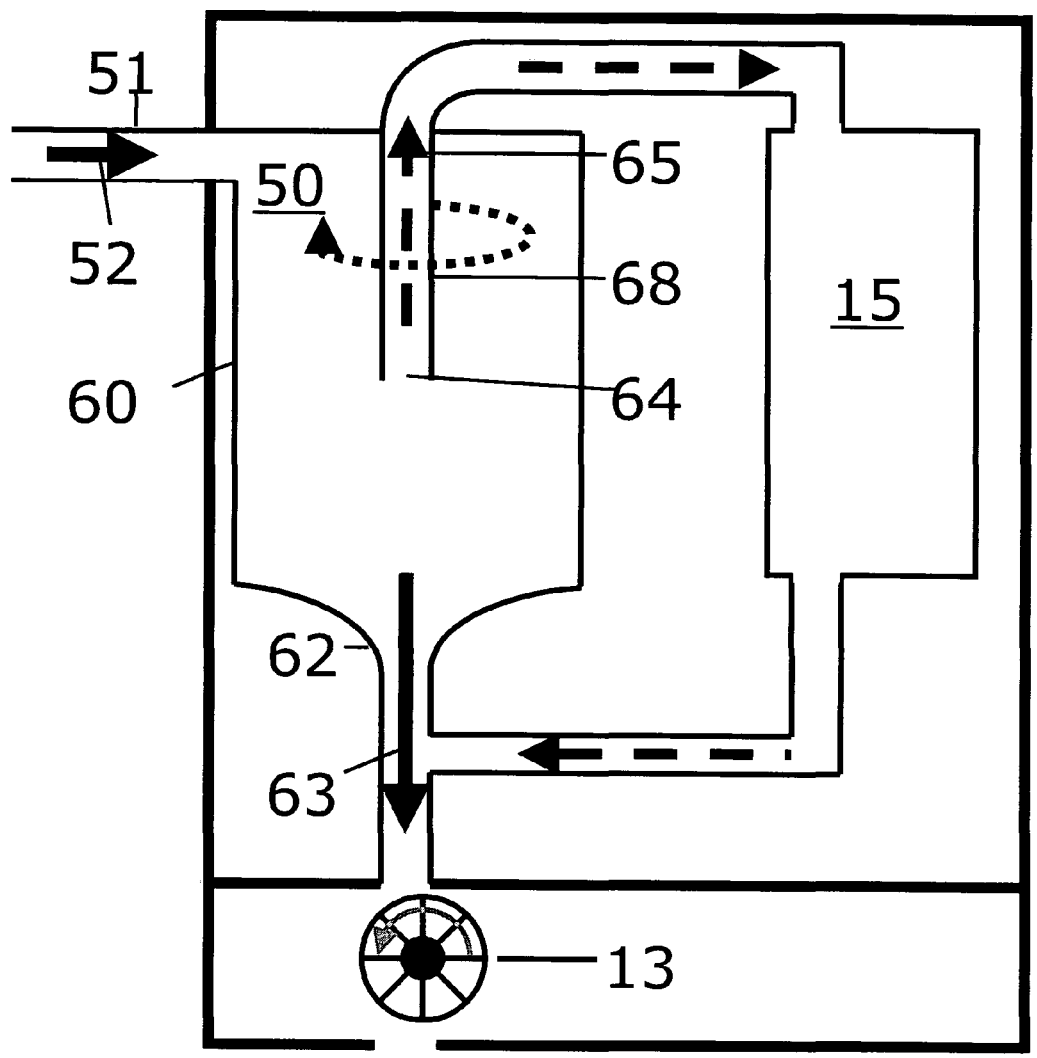
Figure 3C:
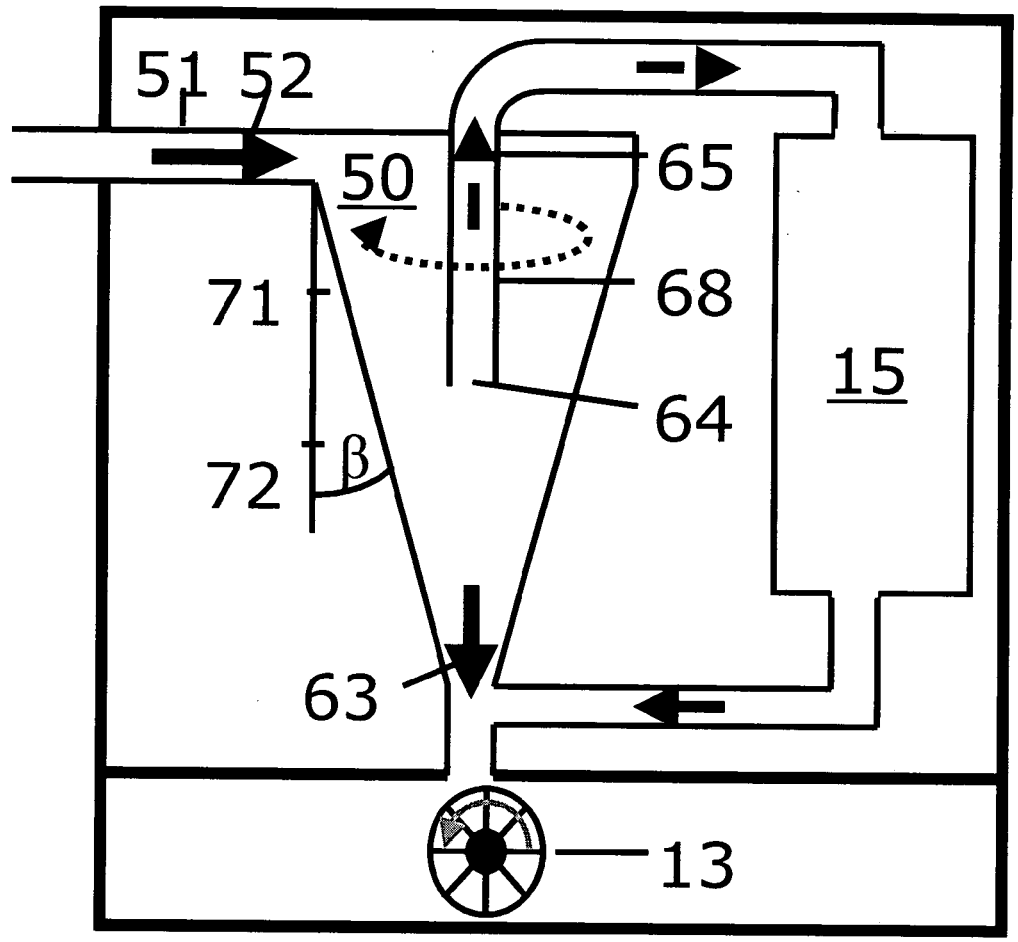
Figure 4:
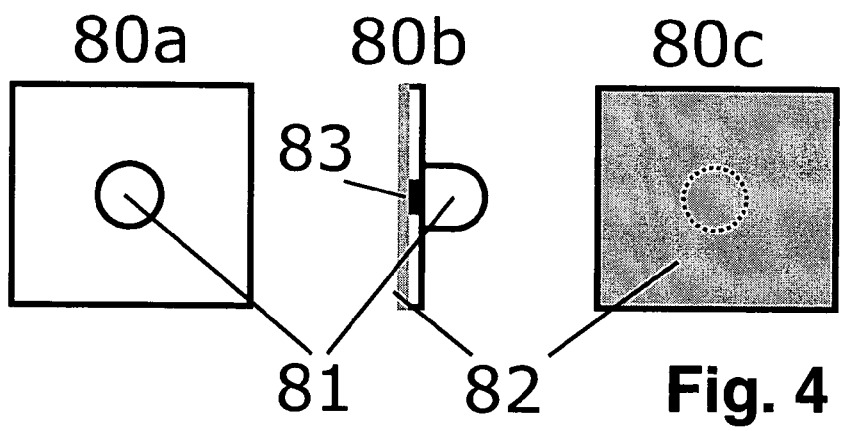
Figure 5:
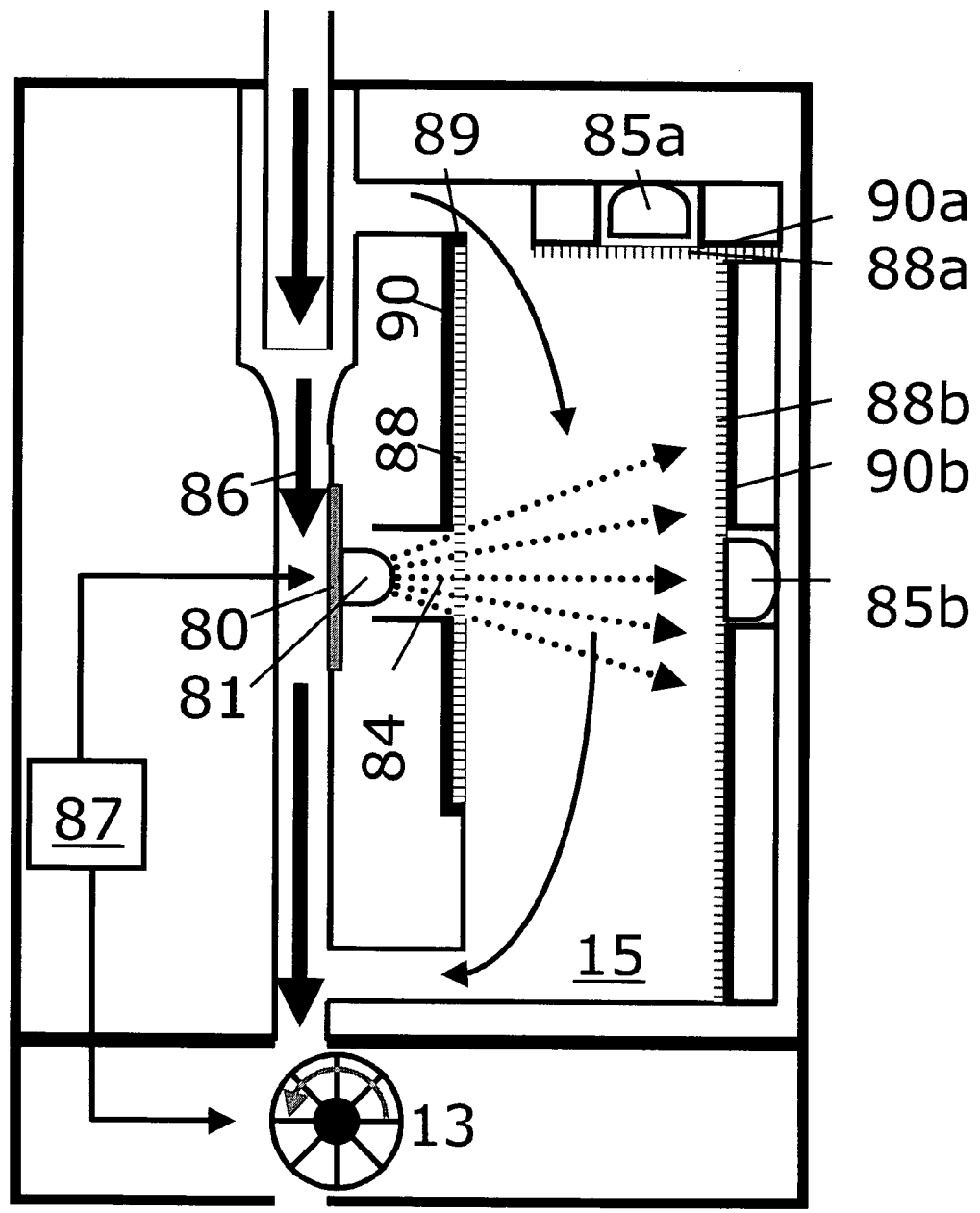
Figure 6:
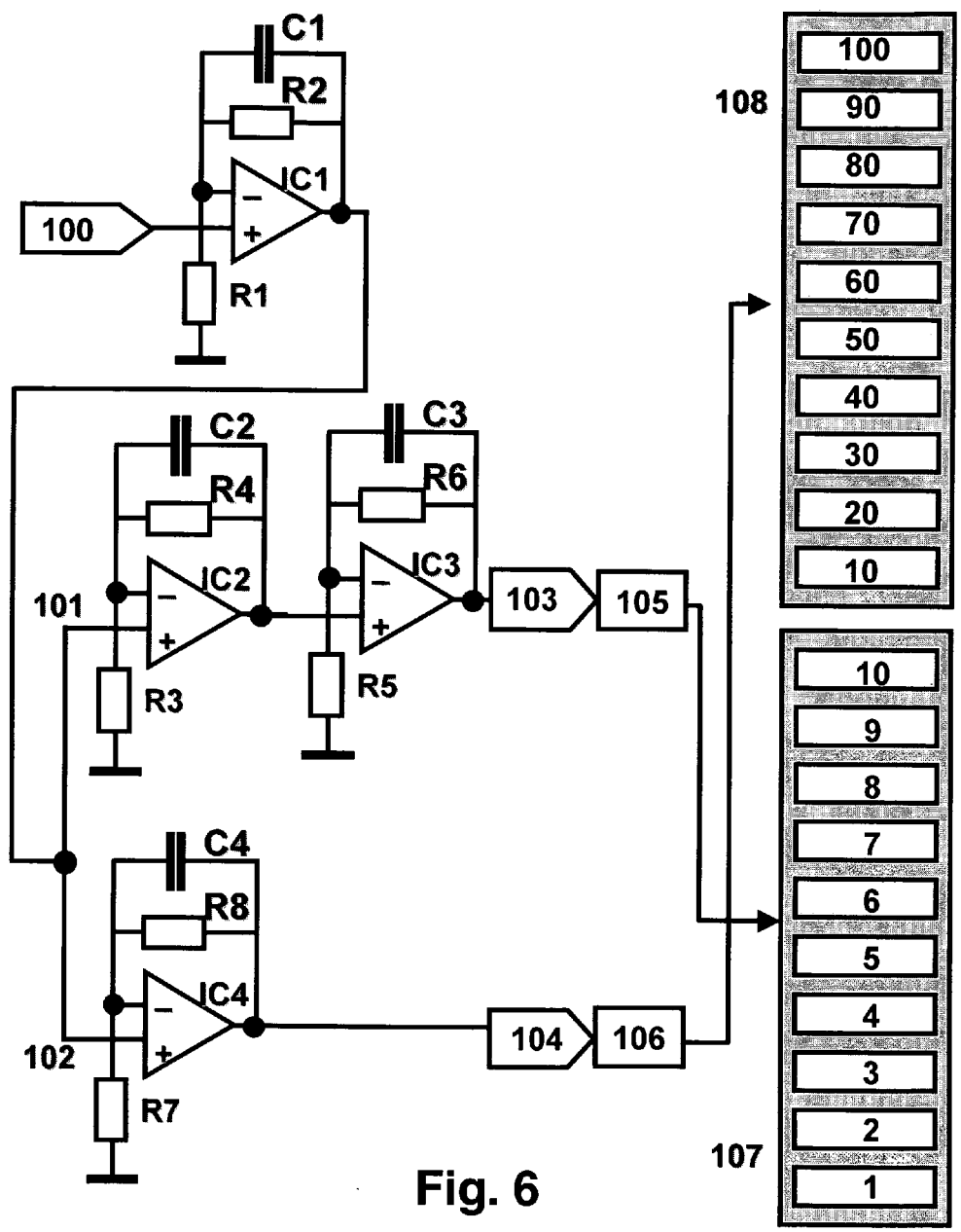
Figure 8A:
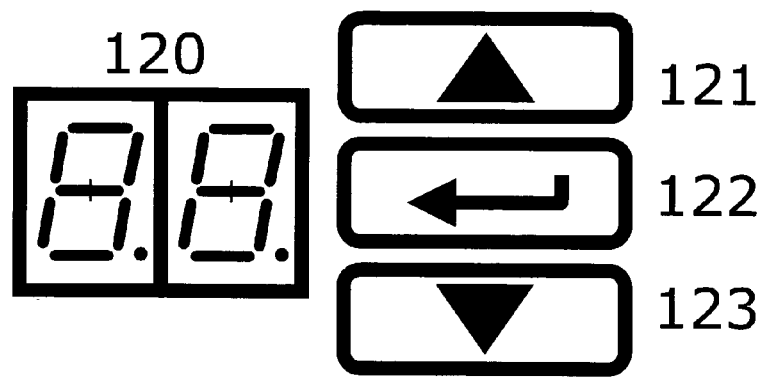
Figure 8B:
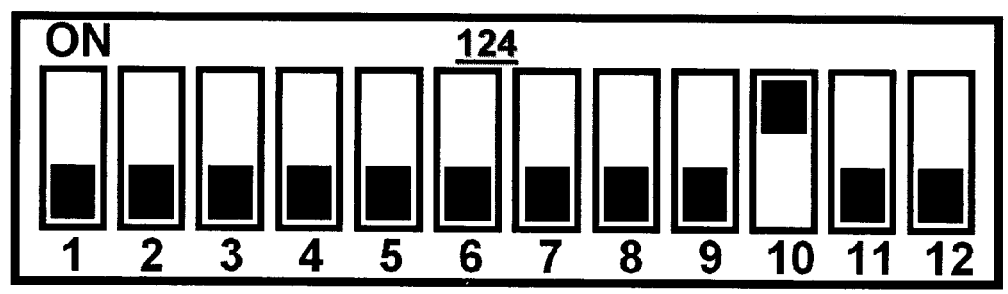

In the following the various aspects of the invention will be explained in detail in conjunction with embodiment examples also depicted in the associated drawing. Depicted in the drawings:

FIG. 1 the basic structure of a fire detection system,

FIG. 2a-2c three embodiment examples of particle separation,

FIG. 3a-3c further embodiment examples of particle separation, wherein FIG. 3a shows a top view and FIGS. 3b and 3c schematic views of two embodiments, FIG. 4 example of a cooled radiation source, FIG. 5 example of the disposition of shieldings, FIG. 6 example of a multi-range amplifier circuit, FIG. 7 table of attainable amplification factors, FIG. 8a-8b two embodiment examples of setting means, and FIG. 9 table for calculating the basic setting of a fire detector.

The particle separation described in the following is distinguished by high throughput, high selectivity and discriminatory power and cost-effective manufacture, and it avoids the disadvantages of the above listed known methods.

The basic concept comprises carrying out a particle separation in a fluid or air system in such a way that only the desired target particles reach the measuring chamber proper.

FIG. 1 shows as an example a fire detector system. The particle separation is here completed so that the air is aspirated by a duct system 11 and subsequently flows into the fire detector device 12. The duct system 11 is comprised of one or more pipes and each has at least one, more often several aspiration ports 14. A pressure differential or low pressure generated by an aspiration mechanism, for example a ventilator 13, causes the inflowing of the air which flows from the aspiration ports across the duct system to the fire detector device 12. Located in the latter is a branching chamber 24. This chamber separates the particles in the aspirated air and only that portion containing the desired target particles is conducted to the measuring chamber 15. This chamber subsequently measures the particle occurrence. The air with all particles leaves the fire detector device 12 via the housing outlet 29. On the device is disposed an interface 16 which, for example, displays measured data or status information and offers setting or data transmission capabilities.

FIG. 1 shows the basic structure. In FIG. 2a a first example is depicted of the particle separation method according to the invention, in which the particle separation according to the invention takes place through acceleration and subsequent deceleration. To the inlet channel 20, here a pipe extending into the branching chamber 24 proper, the pipe system depicted in FIG. 1 is connected. Due to the narrow pipe cross section, which has a lesser inner width than the connected (not shown here) pipe system, the acceleration of the inflowing air takes place. The inlet channel 20 terminates in the lower region of the branching chamber 24. The air, i.e. the total stream, flowing at high velocity from its intake opening maintains the direction but decreases the speed due to the cross section enlargement of the branching chamber in the deceleration region 30 and the expansion capability resulting therefrom. The deceleration of the larger particles contained in the main stream is less than that of the smaller particles, substantially due to the ratio of mass to surface of the particles. Consequently the smaller particles are diverted more easily.

The movement of the fluid, here of the air, is generated by the ventilator 13. The low pressure in the branching chamber 24 is produced, on the one hand, over the path measuring chamber outlet 31, measuring chamber 15 and measuring chamber inlet or measuring chamber branching 26a,' and on the other hand, over the outlet channel 22, wherein the pressure ratios are set so that the slow smaller particles in the side stream move toward the measuring chamber branch 26a, which is here shown at the other end of the branching chamber 24. The latter, however, is not an immutable condition, but rather the measuring chamber branch 26a can also be located in closer proximity to the deceleration region 27 [sic: 30], as is shown in FIG. 2c. Here also a different exit angle α at the measuring chamber branching of approximately 90 degrees is shown, which, for example can be an obtuse angle of approximately 135 degrees, e.g. an acute angle relative to the main stream 21.

From the measuring chamber branching 26a, the side stream 28—now quieted—with the smaller target particles is conducted to the measuring chamber 15. This side stream 28 is considerably smaller than the total stream 21 in the inlet channel 20.

A special advantage is the disposition of the measuring chamber branching 26a at a considerable distance from the deceleration region 30 on the outer wall of the branching chamber 24. This causes the quieting of the flow and it enters, now quieted, the branching channel 32a, which was found to be advantageous for the subsequent measurement in the measuring chamber 15.

The depicted structure effects with high reliability that larger particles remain in the main stream 21 and prevents them from reaching the measuring chamber 15. Only the smaller target particles are conducted to the measuring chamber branching 26a and beyond whose presence and, potentially, whose density is to be determined in the measuring chamber 15.

As stated, the low pressure necessary for the function of the device is generated by the ventilator 13. Since there must be a certain low pressure at the measuring chamber branching 26a in order to draw the side stream into the measuring chamber 15, the ratio of flow velocities in the inlet channel 20 and in the outlet channel 22 is of significance since the low pressure in the measuring chamber region is generated over the measuring chamber outlet 31. It has been found to be advantageous for the cross section of the outlet channel 22 to be smaller than that of the inlet channel 20, preferably approximately half as large.

In order to lend to the main stream 21 at its entrance into the deceleration region 30 as high a velocity as possible, which, as stated above, is essential for good and reliable particle separation, the entrance opening 25 of the inlet channel 20 can be realized as a nozzle, preferably with a clear cross section that is approximately half as large as the clear cross section of the inlet channel 20.

It is furthermore advantageous to implement the discharge opening 27 of the deceleration region 30, which forms the entry of the outlet channel 22, as a funnel-shaped inlet such that it offers the least possible resistance to the main stream 23.

It also appears of significance for the certainty and quality of the separation of main and side stream that in the deceleration region 30 a quasi-congestion occurs before the main stream 23 with the larger particles enters the outlet channel 22.

Located in the measuring chamber 15 is the electronic measuring circuitry and the components, for example optical components, required for this purpose. After the side stream 28 with the target particles has flowed through the measuring chamber 15, it reaches the measuring chamber outlet 31 where it again joins the main stream 23. Together, these streams subsequently reach the aspiration mechanism, the ventilator 13, and thereafter the housing outlet 29.

FIG. 2b represents a variation of the layout shown in FIG. 2a. Here a decisive feature of the invention is also the deceleration region 30, in which the expansion takes place of the entering total fluid stream 21. On the one hand, the branching chamber tapers in the direction of flow of the total stream 21, at least in the deceleration region 30 toward the discharge opening 27. Thus the first substream with the target particles flows from the deceleration region 30 at an angle $\gamma$ to the measuring chamber branching 26b.

The measuring chamber branching 26b is here also implemented differently than in FIG. 2a. The adjoining branch channel 32b is at least approximately shaped in the form of a circular arc with radius r. The transitions are without edges in order to avoid air turbulences and pressure losses. Depending on the separation requirement, also varied is the angle $\gamma$ in the layout and/or the distance from the deceleration region 30 to the measuring chamber branching 26b. If extremely fine particles in the inflowing fluid 21 should be the target particles, the distance from the deceleration region 30 to the measuring chamber branching 26b is selected to be greater and/or the angle $\gamma$ smaller, for example, 10 degrees.

If, for example, the separation of particles smaller than 10 µm is to be attained, larger particles must not reach the measuring chamber 15 and consequently must remain in the main stream. This is necessary, for example, for the detection of fire aerosol particles, for these are, depending on the type of fire, course and measuring time, smaller than 10 µm. To achieve this degree of separation, the ratio between the width and the length of the deceleration region 30 must be 2:1 or ⅕ of the pipe diameter at the entrance opening 25. Subsequently strong acceleration of the fluid takes place immediately through a decrease in cross section in the outlet channel 22. The ratio of the distance 'entrance opening 25 to measuring chamber branching 26b' to the pipe diameter of the inlet channel 20 is approximately 1:1, wherein the angle $\gamma$ should be smaller than 20 degrees. This embodiment example is depicted in FIG. 2b.

FIG. 2c shows a further embodiment in which larger particles of the inflowing fluid 23 also belong to the target particles. The deceleration region 30 itself is different here, in particular narrower and shorter. Also, the distance from the deceleration region 30 to the measuring chamber branching 26c is shorter. In addition, optionally alternatively or additionally, the angle $\gamma$ can be smaller than 90 degrees, for example 70 degrees.

The particle separation is substantially determined by the following factors:
- form/realization of the branching chamber and of the deceleration region 30,
- distance, widening and subsequent tapering of the entrance opening 25 toward the discharge opening 27,
- distance from entrance opening 25 to measuring chamber branching 26,
- pressure differential $\Delta p$ between the entrance opening 25 and the measuring chamber branching 26.

An essential advantage of the described arrangement is the cost-effective manufacture of the branching chamber, since it can have virtually any desired shape. It can be round as well as also square or rectangular which makes manufacturing relatively simple.

FIGS. 3a to 3c show further examples of the particle separation method according to the invention. Here the particle separation takes place by centrifugal forces. In this example as well as in the preceding one, the medium can be a liquid, however also a gas or a gas mixture such as air—in short, a fluid.

It is known that particle separation can also be achieved through a rotational movement and the centrifugal force entailed therein. Herein the particle-containing fluid is set into rotational movement through suitable flow conductance, whereby centrifugal forces act on the heavier, and most often larger, particles, which forces the movement of these particles radially outwardly. The larger particles are consequently pushed toward the outer margin and in the center of the fluid the smaller particles are located. So-called cyclone separators utilize this method for the sequestration of solid as well as liquid particles.

In the present case, however, sequestration of the particles does not take place. The larger particles remain in the main stream of the fluid and subsequently flow out of the device again. A separation takes place and only the fluid with the smaller particles reaches the measuring chamber. This fluid subsequently joins the main stream again and leaves the device.

The function of such a device will be explained in conjunction with FIGS. 3a to 3c, of which FIG. 3a is a top view, the two other Figures representing schematic sectional views.

A container 54, here representing the branching chamber 50, includes an intake opening 53, a measuring chamber branching 55 and a narrowing discharge opening located below with an adjoining outlet channel 62. The latter are evident in FIGS. 3b and 3c.

Into the container 54 flows the fluid 52 tangentially over the intake opening 53, which can be implemented, for example, as a slot inflow. The configuration of the inlet channel 51 and of the container forces the fluid into a circular path 56, e.g. into a rotational flow. In general, the heavier particles, which most often are also the larger ones, move toward the outer wall of the container due to the centrifugal forces acting upon them.

Consequently, only the smaller, lighter particles are located in the center of the container. Here is also located the measuring chamber branching, which is comprised of one pipe 68 with an opening 64. Due to the obtaining pressure differential, only a small quantity of the fluid 65 flows through opening 64 of the measuring chamber branching and subsequently arrives in a measuring chamber 15. Here the quantity or number of the smaller or lighter target particles is measured. Heavier particles do not reach the measuring chamber. The fluid main stream 63 with the heavier particles flows downwardly accelerated by means of the low pressure generated by the ventilator 13. At the bottom, the container 50 has a tapering outlet channel 62, in which the flow velocity of the fluid increases. In addition, laterally disposed at this site is the measuring chamber outlet, in which the required low pressure is generated through the high flow velocity of the exiting main stream 63.

The container 60 can, on the one hand, be cylindrical, as shown in FIG. 3b. On the other hand, it is also feasible to utilize a conical container, such as is shown in FIG. 3c. It is understood that mixed forms are also feasible. If the container has the conical shape shown in FIG. 3c with angle δ [sic], the radius 71 decreases in the direction of flow 63, which causes an increase of the flow velocity of the fluid with the particles. Advantageously the centrifugal forces increase as a result.

During the inflow a so-called spiral inflow is also feasible. Alternatively, also a so-called helical inflow is applicable if the fluid flows perpendicularly to the discharge opening.

In this case the particle separation is essentially determined by the following factors:
diameter and height of the container,
container form,
pipe length of the measuring chamber branching,
opening cross section or diameter of the pipe of the measuring chamber branching,
pressure differential Δp between the opening of the pipe of the measuring chamber branching and the fluid main stream,
flow velocity of the fluid in the container.

The third problem area already addressed above in the measuring and analysis methods and devices under discussion here relates to the light or radiation source disposed in or on the measuring chamber. On the one hand, the necessary cooling must be considered, and on the other hand, the dirt deposits occurring during operation through the accumulation of particles. Both affect the power of the radiation source and thereby the accuracy of the measurement or analysis.

FIGS. 4 and 5 show by example a solution according to the invention which avoids the disadvantages described above.

FIG. 4 shows three views of a light source, here an LED 81, disposed on a board, for example a printed circuit board 80. This printed circuit board with the LED is depicted in FIG. 4 in front view 80a, side view 80b, and in a rear view 80c. The reference numbers are repeated in FIG. 5.

The backside of the printed circuit board 80 functions as a cooling body and for this reason is coated with a thermally conducting material 82. A thermally conducting feed-through 83 enables the heat flow from the light source to the thermally conducting material 82. The heat from the light source consequently is conducted to the backside of the printed circuit board and can be dissipated or transferred further from here.

To optimize the heat dissipation, the backside of the printed circuit board 80—the one with the thermally conducting material 82—is placed in the main stream 86 of the medium or fluid. Stated differently, the main stream of the fluid, which is useless per se, serves for cooling the light or radiation source required for the particle measurement in the side stream. Thus, without further effort or cost the heat output and the cooling of the light source are considerably improved.

A solution according to the invention is depicted in FIG. 5. Here the radiation source 81 outputs its radiation through an opening 84 into the measuring chamber 15. Through radiation obscuration or reflections, for example, caused by particles present, their existence in the medium or fluid can be demonstrated and measured. This is carried out by means of a sensor 85a for measuring radiation reflections and/or of a sensor 85b for measuring the radiation obscuration, e.g. for transmission measurements. Both measurements can also be performed.

To ensure lasting, stable and adequate cooling, a fluid flow 86 must be provided. Should this be omitted—if, for example, the aspiration mechanism 13 is defective—this would negatively impact the service life of the radiation source. Consequently, the stream or the aspiration mechanism should be monitored, which can take place by means of monitoring circuitry 87. This [circuitry] enables the driver current for the light source as long as the aspiration mechanism is running, and generates a corresponding fluid stream. Should the aspiration mechanism fail or no longer operate correctly, the monitoring circuitry blocks or reduces the driver current. Overheating of the radiation source 81 is thus prevented. The monitoring circuitry can represent this state on a local display or transmit this information to an external display.

The problem of particle accumulation already addressed above, which is significantly reduced if not even prevented through the described particle separation, can still be further reduced through additional measures.

In FIG. 5 a number of radiation- or light-permeable shieldings 88, 88a and 88b are disposed. The shielding 88 is located directly in front of the radiation source 81. The shielding 88a is disposed in front of the sensor 85a for reflection measurement and the shielding 88b in front of the sensor 85b for transmission measurement. The shieldings are secured by supports 90, 90a and 90b.

1. The shieldings extend up to the entrance or the start of the measuring chamber where the fluid flows in. They must be of such length that allows potential turbulences to form at the beginning of the shielding and not in the measuring region. These turbulences are caused by the shieldings themselves and the supports necessary for them, whereby unavoidable unevenness, gaps, openings, etc. develop, which through turbulence cause the accumulation of particles in these regions. However, this is outside of the measuring region and therefore has no effect on the measurement.
2. The measuring components, such as for example the radiation sources, sensors, lenses, etc., must be covered. The shieldings must not be discontinuous in these region.
3. The shieldings extend in the direction of flow beyond the region utilized for measurement. Unevenness, gaps, openings, etc., generated here indeed lead again to turbulences and thus to the accumulation of particles. However, this is again outside of the measuring region and therefore has no effect on the measurement. While the shielding 89 in front of the radiation source 81 reduces the radiation quantity that is output into the measuring region—the shielding in front of the sensor also reduces the radiation quantity reaching the sensor—this effect remains constant over the service life since no particles accumulate here. The device can now be appropriately calibrated during its manufacture and in this case has a constant measuring sensitivity during the entire operating time. Recalibration is superfluous.

The problem described in the introduction of too small a measuring range or measuring band is resolved by the invention through an appropriately modified and relatively simple amplifier circuit with expanded dynamic or measuring band range, which is described in the following.

FIG. 6 shows this amplifier circuit. The IC 1 receives the very low input signal 100 from a sensor, normally a few mV or mA or less. This can be, for example, the output signal of a photodiode. This very low signal must now be appropriately amplified in order to be able to process it further. It is tapped at output 103, where it is amplified, as a rule, to several volts. For this purpose most often several operational amplifiers connected in series are utilized. The gain in the operational amplifiers is determined by the ratio of the feedback resistance to the input resistance. Consequently, the amplification of the IC1 is determined by R2/R1, the amplification of the IC2 by R4/R3 and that of the IC3 by R6/R5. Across these three operational amplifiers the very low input signal 100 is amplified to the desired value and is subsequently available at output 103. If the input signal increases further, IC3, starting at a certain input value, goes into saturation and consequently the signal at output 103 cannot increase further. From this point on, the measurement values can no longer be determined.

In the circuit according to FIG. 6 the signal is split following the first amplifier stage IC 1. The output signal of the IC1 is supplied to the IC2 as the input signal 101 (and is conducted subsequently across the IC3 to the output 103) as well as also to the IC4 as the input signal 102. In the IC [sic: 4] the amplification is determined by the ratio R8/R7, which, however, are selected such that the IC4 has a lower amplification than IC2 and IC3 together. While at higher input signals 100 the IC3 goes into saturation, the IC4, however, does not. Consequently, at output 104 of the IC4 subsequently a measuring signal is still present that is referenced to the input signal 100.

On the assumption that all operational amplifiers shown in FIG. 6 have the same amplification factor of 10, the input signal 100 is amplified by the factor 10E3 up to output 103 and by the factor 10E2 up to output 104. Results based on this are included in the Table depicted in FIG. 7. Column T100 represents the value of the input signal 100, column T103 the value of output 103 and column T104 the value of output 104. All values are in mV and it is assumed that the operational amplifier, starting at 10,000 mV, e.g. starting at 10 V, is in saturation. Up to an input value of 10 mV the output 103 has available a greater resolution than output 104. Input values above that, however, can no longer be represented at output 103 due to the saturation. Starting at this point the signal of output 104 is accessed, which can still represent input signals up to 100 mV.

The signal, for example from output 103, can be displayed by means of a converter 105 on a first bar graph display 107. This display indicates the low particle values. The signal of output 104 is, for example also across a converter 106, displayed on a second bar graph display 108. This display indicates the higher particle concentrations.

The two displays 107 and 108 can be provided with the appropriate voltage data in mV from 1 to 10 or from 10 to 100. However, these can represent any other values, or can also be omitted. The two outputs 103 and 104 can be supplied across an analog to digital converter into a microprocessor, where the output signals are further processed. A representation can in this case take place on a local display on the device and/or be transmitted across a data connection in order to represent the signal on an external display or be further processed, for example, in a computer system.

In the introduction, the interface for the basic setting and the initial operation of such a device, in particular a fire detector, was described as the last task in analysis and measuring devices of this type.

A novel setting interface according to the invention prevents errors and reduces the time expenditure for the initial operation of a fire detector and similar devices. As described above in connection with FIG. 1, for the detection and measurement of pollutants in gases and gas mixtures, in particular air, devices 12 are applied which aspirate, via a duct system 11 by means of an aspiration mechanism 13, gas samples and conducts them to a measuring chamber 15 where they are analyzed. As a rule, the duct system has a length between 10 and 200 m and most often has several aspiration ports 14.

The method according to the invention and the corresponding configuration is so simple that erroneous settings, which, it is understood, are particularly critical in the case of fire detectors, can virtually be excluded.

In FIGS. 8a, 8b and 9 details are depicted which will be explained in the following.

On the display 120 depicted in FIG. 8a in the method according to the invention, the number of aspiration ports are set, which, for example by means of a first key 121, each time it is pressed increases the number of aspiration ports by 1, as well as optionally a second key 123, which each time it is pressed decreases the number of aspiration ports by one, as well as an acknowledgment or confirmation key 122 which terminates the input procedure. This display does not absolutely have to be located on the device. It can be implemented as a portable device with a connection plug as well as also as a software solution which runs on a PC and is transmitted to the device by means of a data interface.

In FIG. 8b is depicted a further setting feasibility. A so-called DIP or DIL switch 124 disposed on a printed circuit board has, for example, 12 small switches. If, for example, switch No. 10 is in position ON and all others are at OFF, then in this case 10 aspiration ports are set thereby. After the number of aspiration ports has been set, the trigger and alarm threshold value for a target value of, for example, 5% light obscuration/m for each aspiration port, is calculated as a standard. For this purpose the Table shown in FIG. 9 is stored. In the first line 130 is the target value for each aspiration port. The number of aspiration ports is listed in column 131. The result is calculated by dividing the target value for each aspiration port by the number of aspiration ports. This result can then be found in column 132. In the case of, for example, eight aspiration ports and the standard target value for each aspiration port of 5% light obscuration/m, the measuring chamber must output an alarm signal at a light obscuration value of 0.63.

In addition to units of percent light obscuration per meter, dB/m is also used as a unit. It is understood that the novel setting interface described here functions with both units.

The Table in FIG. 9 shows two further setting feasibilities. At a target value of 8% light obscuration/m for each aspiration port, the triggering of an alarm signal would be delayed; in contrast the triggering would take place earlier at a target value of 2% light obscuration/m for each aspiration port. This is shown in columns 133 or 134. It is understood, that further and different gradation values are feasible.

The above detailed descriptions permit a person of skill in the art to implement further executions of the invention wherein the particle measurement and determination is already significantly improved even if only a portion of the above elements of the invention is applied.

The invention claimed is:

1. A method for the analysis of particles with different properties distributed in a fluid, the method including:
   separating the target particles from the fluid into a first substream and the remaining fluid containing residual particles into a second substream, wherein the target particles are to be analyzed and the residual particles are not to be analyzed;
   exclusively conducting the target particles in the first substream to a measuring chamber;
   analyzing in the measuring chamber the target particles in the first substream;
   cooling a backside of a radiation-emitting or a radiation-receiving component in the measuring chamber with the second substream, such that the residual particles in the second substream do not pass between the radiation-emitting component and the radiation-receiving component; and
   monitoring a flow of the fluid.

2. The method as in claim 1, wherein
   monitoring the flow of the fluid and in the event of a change or failure, changing or reducing the power of at least the radiation-emitting component.

3. The method as in claim 1, wherein after the analysis, the first substream of the fluid with the target particles and the remaining fluid are joined.

4. The method as in claim 1, wherein
   the first substream of the fluid comprising the target particles is smaller than the remaining fluid with the residual particles.

5. The method as in claim 1, wherein
   a predetermined property of the particles is their size, the target particles are separated from the residual particles by means of a method differentiating the size of the particles, and the target particles to be analyzed have a smaller size than the residual particles.

6. The method as in claim 1, wherein
   a predetermined property of the particles is their mass, the target particles are separated from the residual particles by means of a method differentiating the mass of the particles, and the target particles to be analyzed have a lower mass than the residual particles.

7. The method as in claim 1, wherein
   the target particles are separated by means of separation through acceleration from the residual particles.

8. An arrangement for the analysis of particles with different properties distributed in a fluid, the arrangement including:
   a branching chamber in which an inflowing fluid is divided into two substreams with different particle properties, of which a first substream comprises the target particles to be analyzed and a second substream the residual particles; and
   a measuring chamber downstream from the branching chamber with a measuring unit, the first substream with the target particles being conducted into the measuring chamber and these target particles being analyzed by the measuring unit;
   the arrangement configured such that the second substream with the residual particles is conducted whereby at least a portion of this second substream cools the back side of a radiation-emitting or radiation-receiving component;
   the arrangement further configured such that the residual particles in the second substream do not pass between the radiation-emitting component and the radiation-receiving component; and
   a monitoring circuitry for controlling a flow of the fluid.

9. The arrangement as in claim 8, wherein
   the monitoring circuitry which, upon the change or failure of the substream of the fluid serving for cooling, changes or reduces the power of the radiation-emitting component in the measuring chamber.

10. The arrangement as in claim 8, wherein
    the branching chamber comprises a tapering outlet channel through which the second substream of the fluid with heavier-weight particles is discharged.

11. The arrangement as in claim 10, wherein
    after the analysis, the two substreams are joined together by an inlet disposed in the outlet channel for the first substream flowing out of the measuring chamber.

12. The arrangement as in claim 8, wherein
    the branching chamber is implemented as a cyclone separator or a hydrocylone separator having approximately centrally, a branching by which the first substream of the fluid with lighter-weight particles is diverted.

13. The arrangement as in claim 8, wherein
    the branching chamber is implemented as an acceleration system, wherein through a cross sectional enlargement over a short path length two substreams of the fluid are generated of which the first substream comprises the lighter-weight particles while the second substream comprises the heavier-weight particles,
    that a branching is provided through which the first substream of the fluid is diverted and conducted to the measuring chamber.

14. The arrangement as in claim 8, wherein
    in the measuring chamber a radiation source and at least one radiation-sensitive sensor are provided for the determination of the transmission or the reflection of the first substream of the fluid, and
    the radiation source on its back side, located outside of the measuring chamber, is cooled by the second substream.

15. The arrangement as in claim 14, wherein
    in the measuring chamber at least one radiation-permeable or light-permeable shielding is disposed, a first shielding in front of the radiation source and a second shielding in front of a sensor, wherein the shielding extends from the entrance of the measuring chamber beyond the radiation source or the sensor.

16. The arrangement as in claim 8, wherein
    the branching chamber and the measuring chamber and the measuring unit with their radiation-emitting or radiation-receiving component are at least to some extent disposed in a housing which, except for at least one entrance opening and one exit opening, is closed and comprises an aspiration mechanism for generating a low pressure.

17. The arrangement as in claim 8, wherein it is implemented as a fire detector device.

18. An amplifier circuit for use with an arrangement for the analysis as in claim 8, wherein
    several operational amplifiers are provided, of which a first amplifier receives the input signal to be amplified and outputs an amplified output signal,
    this output signal is supplied to a first branch of two or more operational amplifiers, wherein the last operational amplifier, starting at a certain level of the input signal, goes into saturation, and
    the output signal is simultaneously supplied in parallel to a second branch of one or more operational amplifiers, wherein the total gain of the second branch is less than the total gain of the first branch in order for the operational amplifier(s) of the second branch not to reach saturation or to reach saturation later than the last operational amplifier of the first branch.

19. A method for the basic setting or initial operation of an arrangement for the analysis as in claim 8 with several aspiration ports, wherein by means of a first input means the number of aspiration ports is set, subsequently from a stored value table by means of a second input means a target value for a desired light obscuration is selected, and lastly, therefrom the alarm threshold value of light obscuration at which the measuring unit responds is automatically determined.

* * * * *